US00PP09818P

United States Patent [19]

VandenBerg

[11] Patent Number: Plant 9,818

[45] Date of Patent: Mar. 4, 1997

[54] CHRYSANTHEMUM PLANT NAMED 'LAURIE'

[75] Inventor: Cornelis P. VandenBerg, Salinas, Calif.

[73] Assignee: Yoder Brothers, Inc., Barberton, Ohio

[21] Appl. No.: 609,492

[22] Filed: Mar. 1, 1996

[51] Int. Cl.[6] ..... A01H 5/00

[52] U.S. Cl. ..... Plt./78

[58] Field of Search ..... Plt./76, 78, 79

*Primary Examiner*—Howard J. Locker

*Attorney, Agent, or Firm*—Foley & Lardner

[57] ABSTRACT

A Chrysanthemum plant named Laurie particularly characterized by its flat capitulum form; spooned decorative capitulum type; greyed-orange ray floret color; diameter across face of capitulum of 57 to 60 mm when fully opened; branching pattern is spreading and prolific, with 8 to 9 laterals developing after pinch when grown outside under natural daylength in fall flowerings; natural season flower date of August 27 to September 1 when planting rooted cuttings on June 17 to 18 in Salinas, Calif. and of October 10 to 17 when planting rooted cuttings June 15 to 18 in Hightstown, N.J.; plant height of 28 to 38 cm when grown in fall under natural daylength with no growth regulators; and durable, uniform performance.

3 Drawing Sheets

The present invention comprises a new and distinct cultivar of Chrysanthemum, botanically known as *Dendranthema grandiflora,* and referred to by the cultivar name Laurie.

Laurie, identified as 8565 (92-601002), was originated from an open pollination program, where the best breeding lines were selected by Cornelis P. VandenBerg, flowered under controlled conditions outdoors and left to be pollinated by bees, in Salinas, Calif., in September of 1991.

The female parent of Laurie was an unnamed seedling, identified as 8076 (85-018002), and described as a garden mum with a spooned daisy flower form and a pink flower color. The female parent was discarded in October of 1991.

The male parent of Laurie is unknown, since the female parent of Laurie was open pollinated.

Laurie was discovered and selected as one flowering plant within the progeny of the stated cross by Cornelis P. VandenBerg in October of 1992 in a controlled environment in Salinas, Calif.

The first act of asexual reproduction of Laurie was accomplished when vegetative cuttings were taken from the initial selection in December of 1992 in a controlled environment in Salinas, Calif., by technicians working under the supervision of Cornelis P. VandenBerg.

Horticultural examination of controlled flowerings of successive plantings has shown that the unique combination of characteristics as herein disclosed for Laurie are firmly fixed and are retained through successive generations of asexual reproduction.

Laurie has not been observed under all possible environmental conditions. The phenotype may vary significantly with variations in environment such as temperature, light intensity and daylength, without, however, any variance in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October.

The following traits have been repeatedly observed and are determined to be basic characteristics of Laurie, which, in combination, distinguish this Chrysanthemum as a new and distinct cultivar:

1. Flat capitulum form.
2. Spooned decorative capitulum type.
3. Greyed-orange ray floret color.
4. Diameter across face of capitulum of 57 to 60 mm when fully opened.

5. Branching pattern is spreading and prolific, with 8 to 9 laterals developing after pinch when grown outside under natural daylength in fall flowerings.
6. Natural season flower date of August 27 to September 1 when planting rooted cuttings on June 17 to 18 in Salinas, Calif., and of October 10 to 17 when planting rooted cuttings June 15 to 18 in Hightstown, N.J.
7. Plant height of 28 to 38 cm when grown in fall under natural daylength with no growth regulators.
8. Durable, uniform performance.

The accompanying photographic drawings show typical inflorescence and leaf characteristics of Laurie, with the colors being as nearly true as possible with illustrations of this type.

Sheet 1 is a color photograph of Laurie grown in natural season outside conditions in salinas, Calif.

Sheet 2 is a black and white photograph of three views of the inflorescence of Laurie.

Sheet 3 is a black and white photograph showing the upper and under sides of the leaves of Laurie at 3 stages of development (mature, intermediate and immature).

In sheets 2 and 3 a measuring tape in centimeters has been added.

Of the commercial cultivars known to the inventor, the most similar in comparision to Laurie is the cultivar identified as Triumph, disclosed in U.S. Pat. No. P.P. 5,995. Reference is made to attached Chart A, which compares certain characteristics of Laurie to the same characteristics of Triumph.

Similar traits are capitulum form and type, and branching pattern. The ray floret color of Laurie is greyed-orange (R.H.S. between 22A and 163C), the ray floret color of Triumph is described as yellow-orange (R.H.S. 22A to 22B). Laurie has a smaller diameter of capitulum, a much slower natural season flowering response, and a taller plant height when compared with Triumph. In addition, Laurie has ray florets with long corolla tubes and spatulate ray floret tips, while Triumph has ray florets with medium length corolla tubes.

In the following description color references are made to The Royal Horticultural Society Colour Chart. The color values were determined on plant material grown as a pinched garden mum grown outdoors in Salinas, Calif. on Sep. 1, 1995.

Classification:

*Botanical.*—*Dendranthema grandiflora* cv Laurie.

*Commercial.*—Flat spooned decorative garden mum.

INFLORESCENCE

A. Capitulum:
*Form.*—Flat.
*Type.*—Spooned decorative.
*Diameter across face.*—57 to 60 mm when fully opened.

B. Corolla of ray florets:
*Color (General tonality from a distance of three meters).*—Greyed-orange.
*Color (upper surface).*—Between 22A and 163C.
*Color (under surface).*—22A to 22B.
*Shape.*—Straight, with long corolla tube and spatulate ray floret tip.

C. Corolla of disc florets:
*Color (mature).*—14B.
*Color (immature).*—14B, overlaid with 144B.

D. Reproductive organs:
*Androecium.*—Present on disc florets only; no pollen.
*Gynoecium.*—Present on both ray and disc florets.

PLANT

A. General appearance:
*Height.*—28 to 38 cm when grown in fall under natural daylength with no growth regulators.
*Branching pattern.*—Spreading and prolific.

B. Foliage:
*Color (upper surface).*—147A.
*Color (under surface).*—147B.
*Shape.*—Small, deeply lobed and serrated.

CHART A

| CULTIVAR | LAURIE | TRIUMPH |
|---|---|---|
| Ray floret color | Greyed-orange | Yellow-orange |
| Capitulum form and type | Flat decorative | Flat decorative |
| Diameter across face of capitulum | 57 to 60 mm | 64 to 80 mm |
| Branching pattern | Spreading | Spreading |
| Nat. season flower date: | | |
| in Salinas, CA | Aug 27 to Sep 1 | Aug 8 to 16 |
| in Hightstown, NJ | Oct 10 to 17 | Sep 23 to 28 |
| Plant height | 28 to 38 cm | 23 to 28 cm |

COMPARISONS MADE OF PLANTS GROWN UNDER NATURAL SEASON OUTDOOR CONDITIONS IN SALINAS, CALIFORNIA AND IN HIGHTSTOWN, NEW JERSEY

What is claimed is:

1. A new and distinct Chrysanthemum plant named Laurie, as described and illustrated.

* * * * *

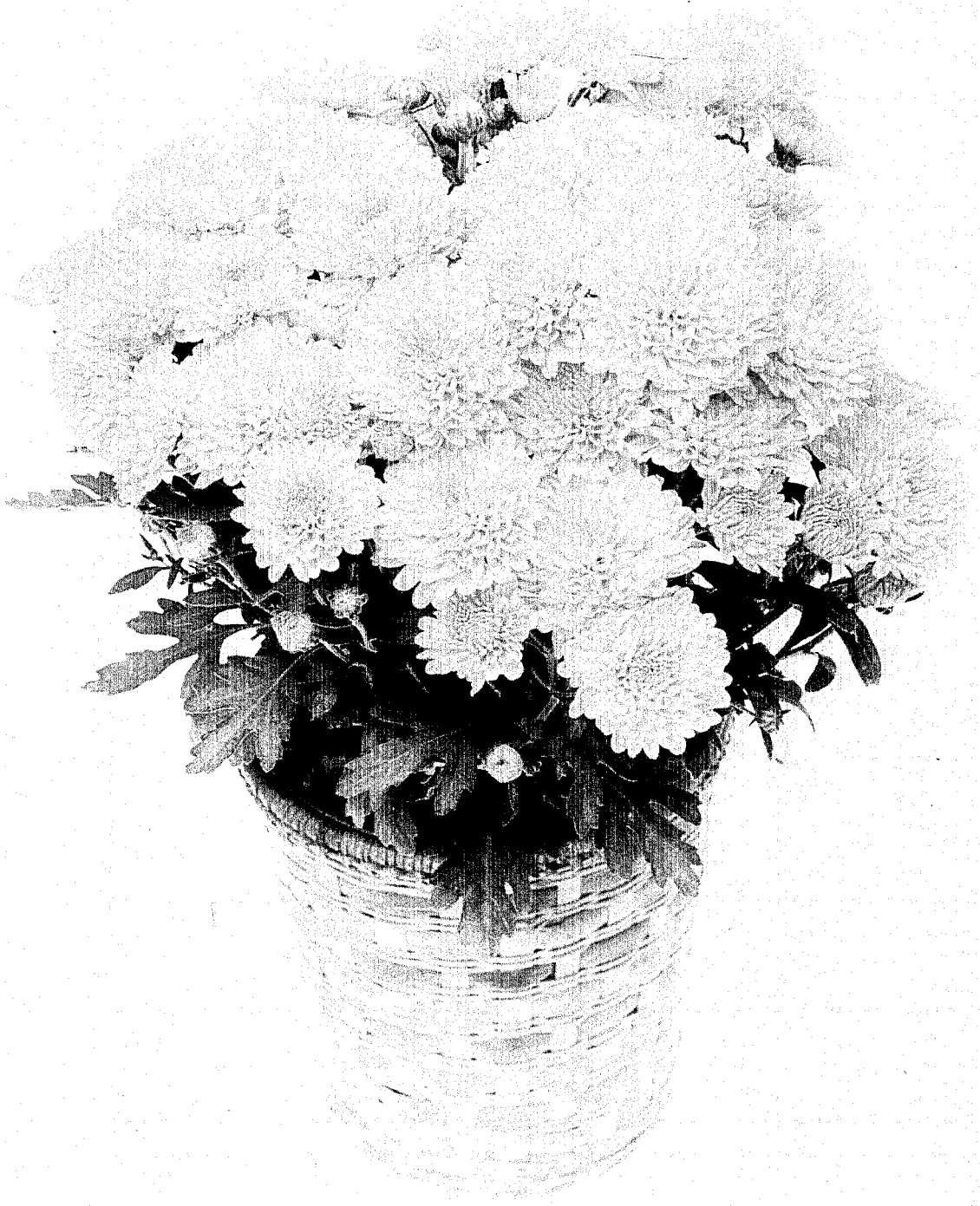

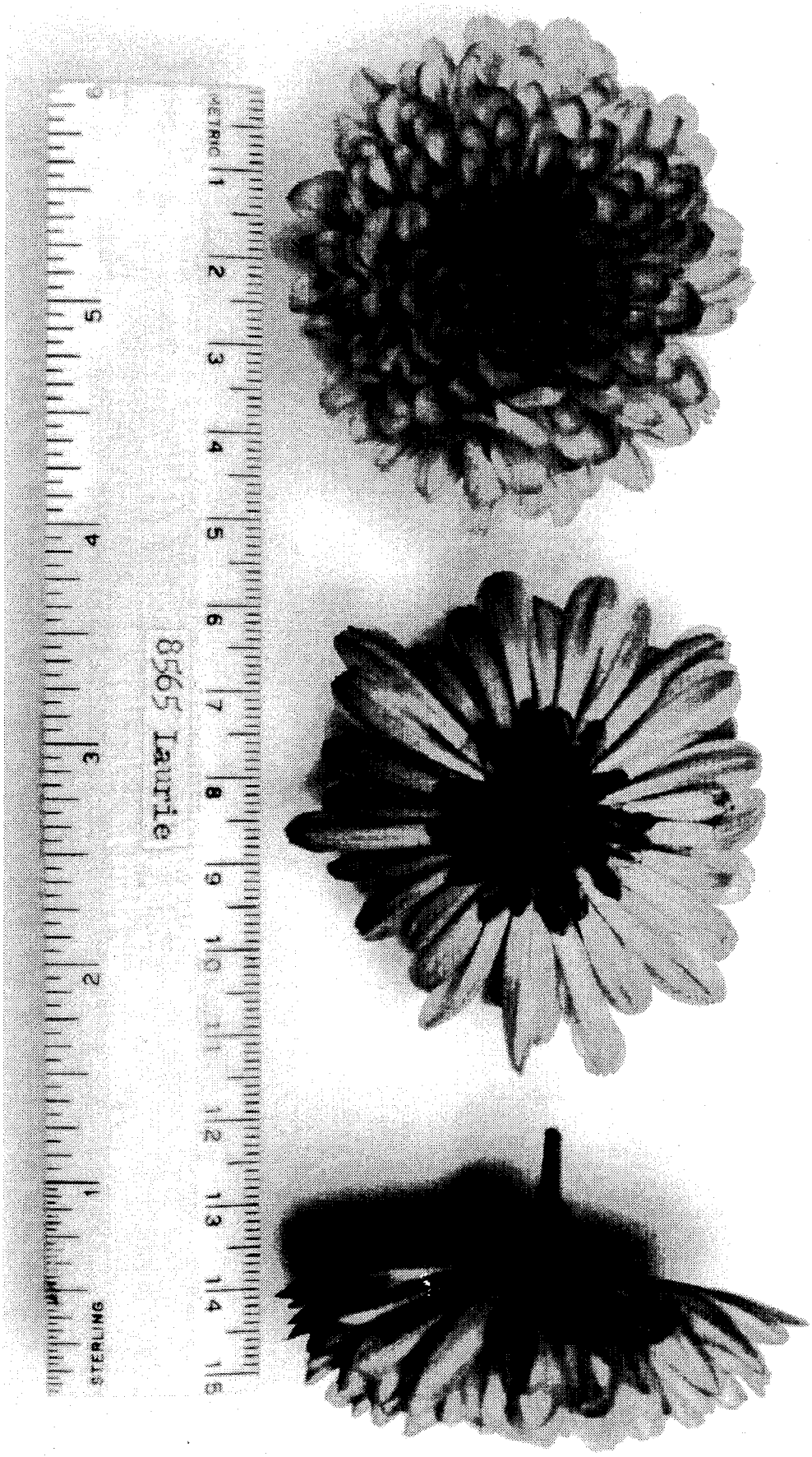
8565 Laurie
STERLING
METRIC

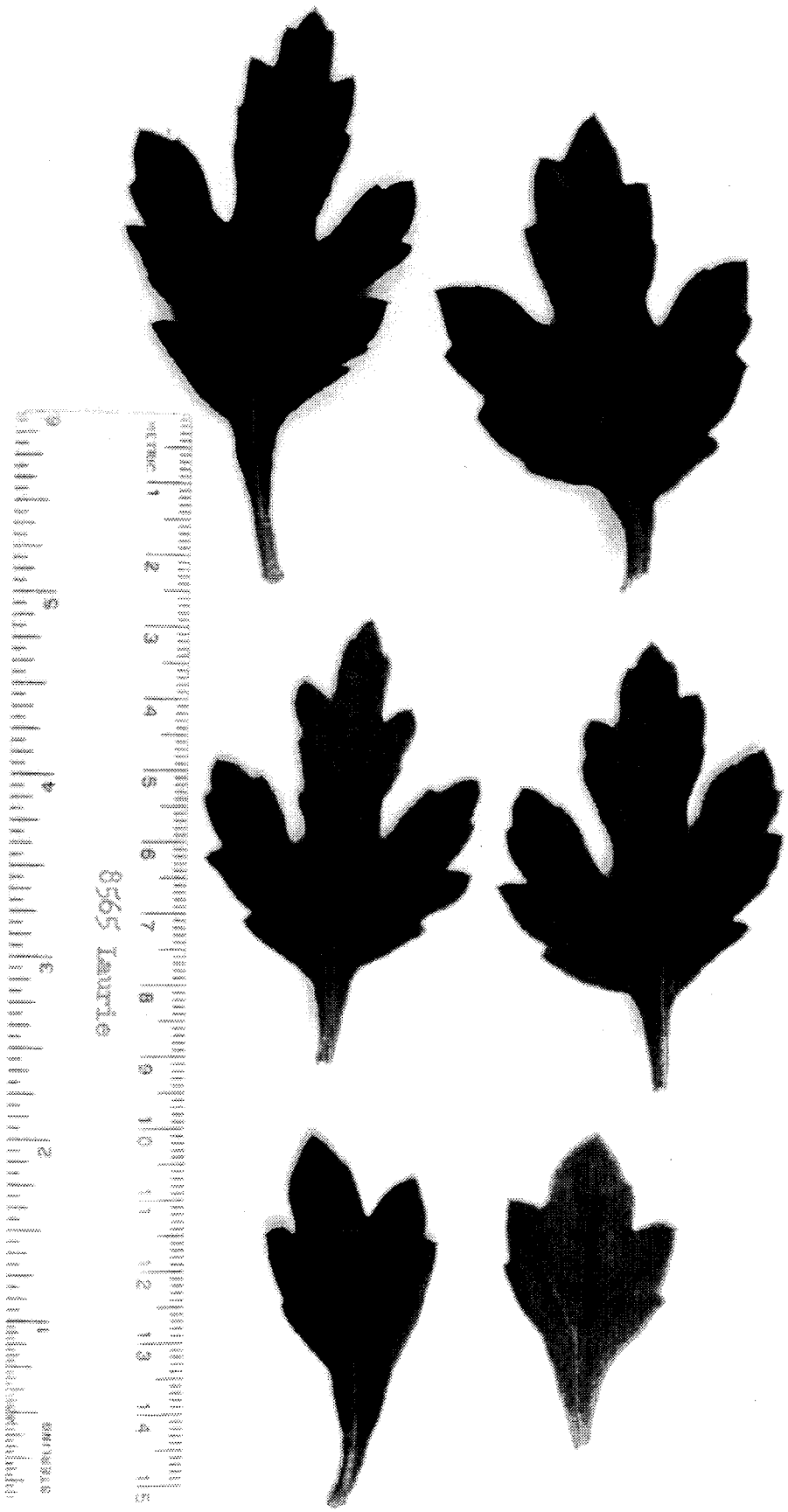
8565 Laurie